US00PP17304P2

(12) United States Plant Patent
Pierce

(10) Patent No.: US PP17,304 P2
(45) Date of Patent: Dec. 26, 2006

(54) *CALIBRACHOA* PLANT NAMED 'CAL CORINK'

(50) Latin Name: ***Calibrachoa* sp.**
Varietal Denomination: Cal Corink

(75) Inventor: Robert Osteen Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 64 days.

(21) Appl. No.: 11/352,594

(22) Filed: Feb. 13, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—Annette H Para
(74) *Attorney, Agent, or Firm*—Jondle & Associates P.C.

(57) ABSTRACT

A new *Calibrachoa* plant particularly distinguished by medium to large coral-pink flowers with red markings, early and continuous flowering, medium green foliage with small lanceolate leaves, and a moderately-vigorous, round, bushy, medium tight plant habit, and an initially spreading and later prostrate or trailing plant habit, is disclosed.

2 Drawing Sheets

Genus and species: *Calibrachoa* sp.
Variety denomination: 'Cal Corink'.

BACKGROUND OF THE NEW PLANT

The present invention comprises a new and distinct cultivar of *Calibrachoa,* botanically known as *Calibrachoa* sp., and hereinafter referred to by the cultivar name 'Cal Corink'. The new cultivar originated from a hybridization made in November 2002 in Gilroy, Calif. The female parent was the proprietary light-orange flowered *Calibrachoa* plant '111' (unpatented), while the male parent was the proprietary *Calibrachoa* plant '144' (unpatented) having cherry-red flowers. The seeds produced by the hybridization were sown in January 2003 in Gilroy, Calif. A single plant selection was chosen for further evaluation and for asexual propagation in summer 2003 in Gilroy, Calif.

The new cultivar was created in 2003 in Gilroy, Calif. and has been asexually reproduced repeatedly by vegetative cuttings and tissue culture in Gilroy, Calif. over a two-year period. 'Cal Corink' has not been observed under all possible environmental conditions. The present invention has been found to retain its distinctive characteristics through successive asexual propagations.

Plant Breeder's Rights for this cultivar were applied for in Canada on Jul. 19, 2005, in Switzerland on Sep. 16, 2005 and with the European Union on Sep. 28, 2005.

SUMMARY OF THE INVENTION

The following are the most outstanding and distinguishing characteristics of this new cultivar when grown under normal horticultural practices in Gilroy, Calif. and Hillscheid, Germany.

1. Medium to large, coral-pink flowers with red markings;
2. Medium-green foliage with small, lanceolate leaves;
3. A medium to larger size, moderately vigorous, round, bushy, and moderately tight plant habit;
4. An initially spreading to later prostrate or trailing habit; and
5. An early and continuous flowering response.

DESCRIPTION OF PHOTOGRAPHS

This new *Calibrachoa* plant is illustrated by the accompanying photographs which show overall plant habit including blooms, buds, and foliage of the plant; the colors shown are as true as can be reasonably obtained by conventional photographic procedures. The photographs are of a whole plant grown in a greenhouse in Hillscheid, Germany, in May of 2005.

DESCRIPTION OF THE NEW CULTIVAR

Figure 1:
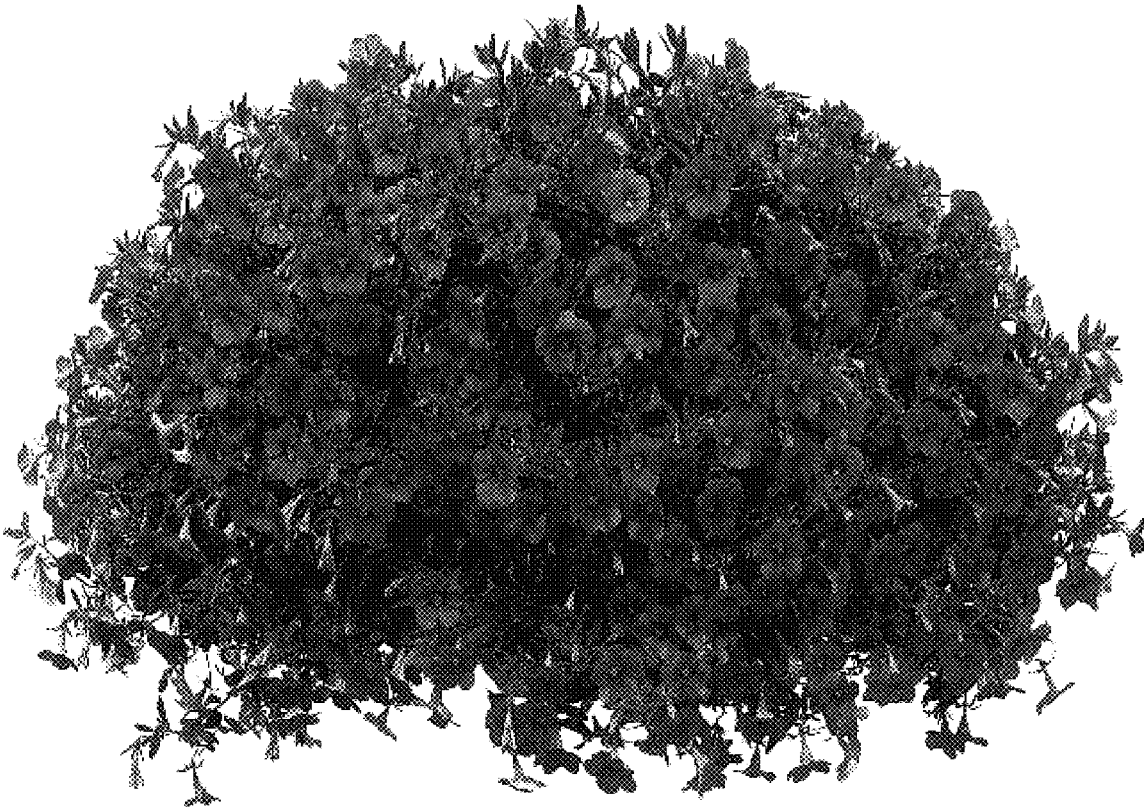
FIG. 1 shows the overall plant habit, including blooms, buds and foliage of a 25-week old plant.
Figure 2:
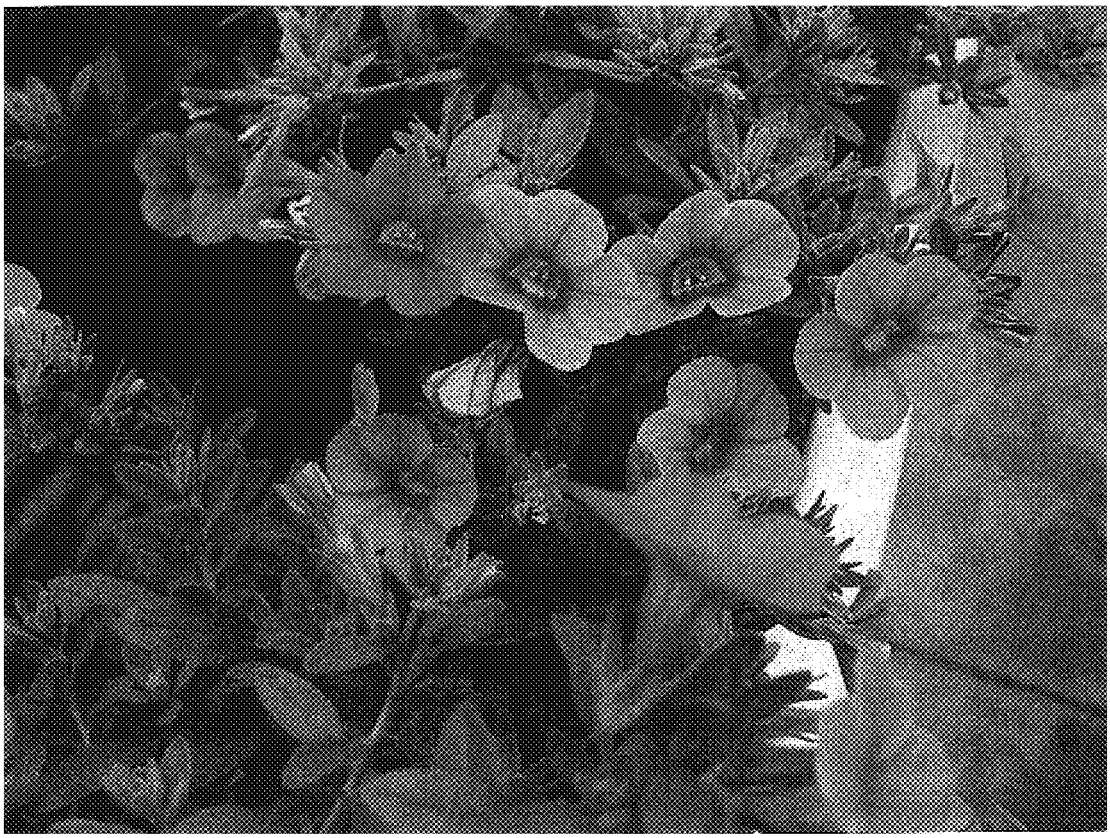
FIG. 2 shows a close-up of the mature inflorescences of an 11-week old plant.

The following detailed description sets forth the distinctive characteristics of 'Cal Corink'. The data which define these characteristics were collected from asexual reproductions carried out in Hillscheid, Germany. The plant history was taken on 6-week old unpinched plants which were planted as rooted cuttings in 12-cm pots in mid-July 2005, and then grown in a greenhouse. Observations were made when the plants were in full flower in August 2005. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Solanaceae.
*Botanical.*—*Calibrachoa* sp.
*Common name.*—*Calibrachoa.*

Parentage:
*Female parent.*—'111' a proprietary light-orange flowered *Calibrachoa* plant (unpatented).
*Male parent.*—'144', a proprietary light-cherry flowered *Calibrachoa* plant (unpatented).

Growth:

*Form.*—Herbaceous perennial, usually cultivated as an annual plant.

*Habit.*—Spreading initially, decumbent or trailing plant habit later; fair branching; develops into a round, moderately tight habit.

*Height* (*measured from the top of the soil*).—12.8 cm.

*Width* (*horizontal plant diameter*).—46.2 cm.

*Propagation.*—Terminal tips for cuttings.

*Time to produce a finished flowering plant.*—9 to 10 weeks for a 12-cm pot.

*Outdoor plant performance.*—For hanging baskets and containers.

*Time to initiate and develop roots.*—About 24 days.

*Root description.*—Fibrous, self-branching.

Stems:

*Average number* (*basal plus secondary*).—10.4.

*Length of basal branches* (*from the base of the stem to the tip*).—27 cm.

*Internode length.*—1.0 cm to 2.5 cm.

*Diameter of branches* (*from midpoint*).—0.2 cm to 0.3 cm.

*Stem color.*—RHS 143B, partly infused with anthocyanin that is RHS 174A or lighter.

*Texture.*—Somewhat rough, covered with hair.

Leaves:

*Arrangement.*—Initially alternate, later opposite or nearly opposite on the flowering branches.

*Size.*—Length: 3.5 cm. Width: 1.1 cm.

*Shape.*—Lanceolate to narrowly elliptic.

*Margin.*—Entire.

*Apex.*—Obtuse.

*Base.*—Attenuate.

*Color* (*mature leaves*).—Upper surface: RHS 137C (medium green). Lower surface: RHS 138A to RHS 138B.

*Texture.*—Velvety, very fine pubescence.

*Venation.*—Pinnate (indistinct).

*Venation color.*—RHS 145B for the midrib of the lower surface.

*Variegation.*—None.

*Petioles.*—Length: 0.3 cm to 0.5 cm. Width: 0.2 cm. Color: RHS 145A. Texture: Hair along the edge.

Flower bud:

*Shape.*—Tube-shaped to narrow funnel-shaped.

*Size.*—Length: 2.2 cm. Diameter: 0.5 cm to 0.6 cm.

*Color at tight bud.*—Main part is RHS 60A (ochre) with RHS 55B at the tips.

Inflorescence:

*Blooming habit.*—Continuous from Spring to late Fall.

*Inflorescence type.*—Flowers appear solitary, emerging from the leaf axil.

*Floret type.*—Base is funnel-shaped; corolla lobes are salver-shaped.

*Number of flowers per node.*—One.

*Lastingness of individual blooms on the plant.*—6 days.

*Size.*—Width (flower face): 3.1 cm to 3.3 cm. Length: (flower face): 2.8 cm to 3.0 cm. Depth (total length of flower): 2.3 cm.

*Funnel.*—Length (from below): 2.0 cm. Diameter (at opening): Up to 1.1 cm.

*Fragrance.*—Weak, petunia-like.

*Peduncles.*—Color: RHS 137C (green) or RHS 146D (green). Length: 2.5 cm to 3.5 cm. Diameter: 0.1 cm. Texture: Covered with dense pubescence.

Flowers:

*Immature flower.*—Diameter: 2.6 cm. Color: RHS 58B (deep rose-red).

*Mature flower color.*—RHS 52B, may slightly fade, with an RHS 46B (red) to RHS 46C (red) ring around the funnel opening.

*Corolla.*—Shape of corolla: Tube-shaped. Color inside: RHS 12B (yellow) with RHS 12A (deeper yellow) patch at the opening. Color outside: RHS 162B (ochre-yellow), with fine, indistinct veins. Outside texture: Weakly furrowed with hair along the veins.

*Petals.*—Shape: Lower part is fused and upper part is a free lobe. Apex: Weakly rounded. Base: Fused. Margin: Entire. Waviness of petals: Absent or very weak. Lobation: Medium. Texture: Smooth.

*Sepals.*—Shape: Ensiform. Apex: Acute. Base: Fused. Margin: Entire. Length: 1.4 cm. Width: 0.2 cm to 0.3 cm. Color: RHS 143B (green). Texture: Pubescent (covered with dense hair). Pubescence color: Whitish.

Reproductive organs:

*Stamens.*—Number: 5 (various lengths). Filament color: RHS 155A (whitish). Filament length: 0.9 cm to 1.4 cm. Filament diameter: 0.1 cm. Pollen color: RHS 6D (pale-yellow). Pollen quantity: Moderate.

*Pistils.*—Number: 1. Length: 1.3 cm. Diameter: 0.1 cm. Stigma color: RHS 143C (light-green). Style color: RHS 145B (pale-green).

Fruit and seed set: No seed set observed.

Disease and insect resistance: No particular resistance or susceptibility has been observed.

COMPARISON WITH PARENTAL AND COMMERCIAL CULTIVARS

'Cal Corink' differs from the female parent '111' (unpatented), by having coral-pink flowers, while '111' has light-orange flowers. In addition, 'Cal Corink' has darker green leaves and an earlier flowering response than '111'.

'Cal Corink' differs from the male parent '144' (unpatented), by having coral-pink flowers, while '144' has cherry-red flowers. In addition, 'Cal Corink' has smaller leaves and more basal branching than '144'.

'Cal Corink' differs from the commercial cultivar 'Cal Pink' (U.S. Plant Pat. No. 14,496), by having smaller leaves, lighter green foliage and a lighter anthocyanin color in the stems than 'Cal Pink'.

I claim:

1. A new and distinct cultivar of *Calibrachoa* plant as shown and described herein.

* * * * *